United States Patent
Fine et al.

[11] Patent Number: 6,031,603
[45] Date of Patent: Feb. 29, 2000

[54] SENSOR, METHOD AND DEVICE FOR OPTICAL BLOOD OXIMETRY

[75] Inventors: Ilya Fine, Rehovot; Alexander Sternberg, Haifa; Yeshayahu Katz, Haifa; Leonid Goldinov, Haifa; Boris Rapoport, Kiryat Ata, all of Israel

[73] Assignee: Cybro Medical, Ltd., Haifa, Israel

[21] Appl. No.: 08/973,709

[22] PCT Filed: Jun. 6, 1996

[86] PCT No.: PCT/IL96/00006

§ 371 Date: Jul. 9, 1998

§ 102(e) Date: Jul. 9, 1998

[87] PCT Pub. No.: WO96/41566

PCT Pub. Date: Dec. 27, 1996

[30] Foreign Application Priority Data

Jun. 9, 1995 [IL] Israel ........................................ 114080
Jun. 9, 1995 [IL] Israel ........................................ 114082

[51] Int. Cl.⁷ .............................. G01B 11/02; A61B 8/14
[52] U.S. Cl. .............................................. 356/41; 128/633
[58] Field of Search .................................. 356/39, 40, 41; 128/633, 664, 665; 600/310, 314–316, 322–324, 326, 328, 340

[56] References Cited

U.S. PATENT DOCUMENTS

| | | | |
|---|---|---|---|
| 4,112,923 | 9/1997 | Tomeck | 128/13 |
| 4,167,331 | 9/1979 | Nielsen | 356/39 |
| 4,224,948 | 9/1980 | Cramer et al. | 128/690 |
| 4,449,535 | 5/1984 | Renault | 128/634 |
| 4,485,820 | 12/1984 | Flower | 128/633 |
| 4,729,385 | 3/1988 | Juncosa et al. | 128/734 |
| 4,796,636 | 1/1989 | Branstetter et al. | 128/633 |
| 4,938,218 | 7/1990 | Goodman et al. | 128/633 |
| 5,063,932 | 11/1991 | Dahl et al. | 128/633 |
| 5,090,415 | 2/1992 | Yamashita et al. | 128/665 |
| 5,099,842 | 3/1992 | Mannheimer et al. | 128/633 |
| 5,131,391 | 7/1992 | Sakai et al. | 128/633 |
| 5,137,355 | 8/1992 | Barbour et al. | 356/342 |
| 5,203,329 | 4/1993 | Takatani et al. | 128/633 |
| 5,224,478 | 7/1993 | Sakai et al. | 128/633 |
| 5,228,440 | 7/1993 | Chung et al. | 128/633 |
| 5,247,932 | 9/1993 | Chung et al. | 128/633 |
| 5,280,788 | 1/1994 | Janes et al. | 128/665 |
| 5,284,149 | 2/1994 | DhadwaL et al. | 128/665 |
| 5,309,907 | 5/1994 | Fang et al. | 128/633 |
| 5,345,935 | 9/1994 | Hirsch et al. | 128/642 |
| 5,351,686 | 10/1994 | Steuer et al. | 128/633 |
| 5,419,321 | 5/1995 | Evans | 128/633 |
| 5,422,197 | 7/1995 | Stark | 128/633 |
| 5,456,253 | 10/1995 | Steuer et al. | 128/633 |
| 5,490,506 | 2/1996 | Takatani et al. | 128/633 |
| 5,513,642 | 5/1996 | Ostrander | 128/633 |
| 5,517,987 | 5/1996 | Tsuchiya | 128/633 |
| 5,529,065 | 6/1996 | Tsuchiya | 128/633 |

FOREIGN PATENT DOCUMENTS 2 075 668  11/1991  United Kingdom .

*Primary Examiner*—Frank G. Font
*Assistant Examiner*—Michael P. Stafira

[57] ABSTRACT

There is described a new sensor for optical blood oximetry as well as a method and apparatus in which the new sensor is used. The new sensor includes two point-like light emitters (23,24) positioned in the center of the device in close proximity to each other and at least one and preferably two annular detector terminals (32,39) concentrically surrounding the light emitters. The light sources may, for example, be two laser diodes emitting each monochromatic light within the range of 670 nm to 940 nm. The detector devices are, for example, photodetectors.

31 Claims, 4 Drawing Sheets

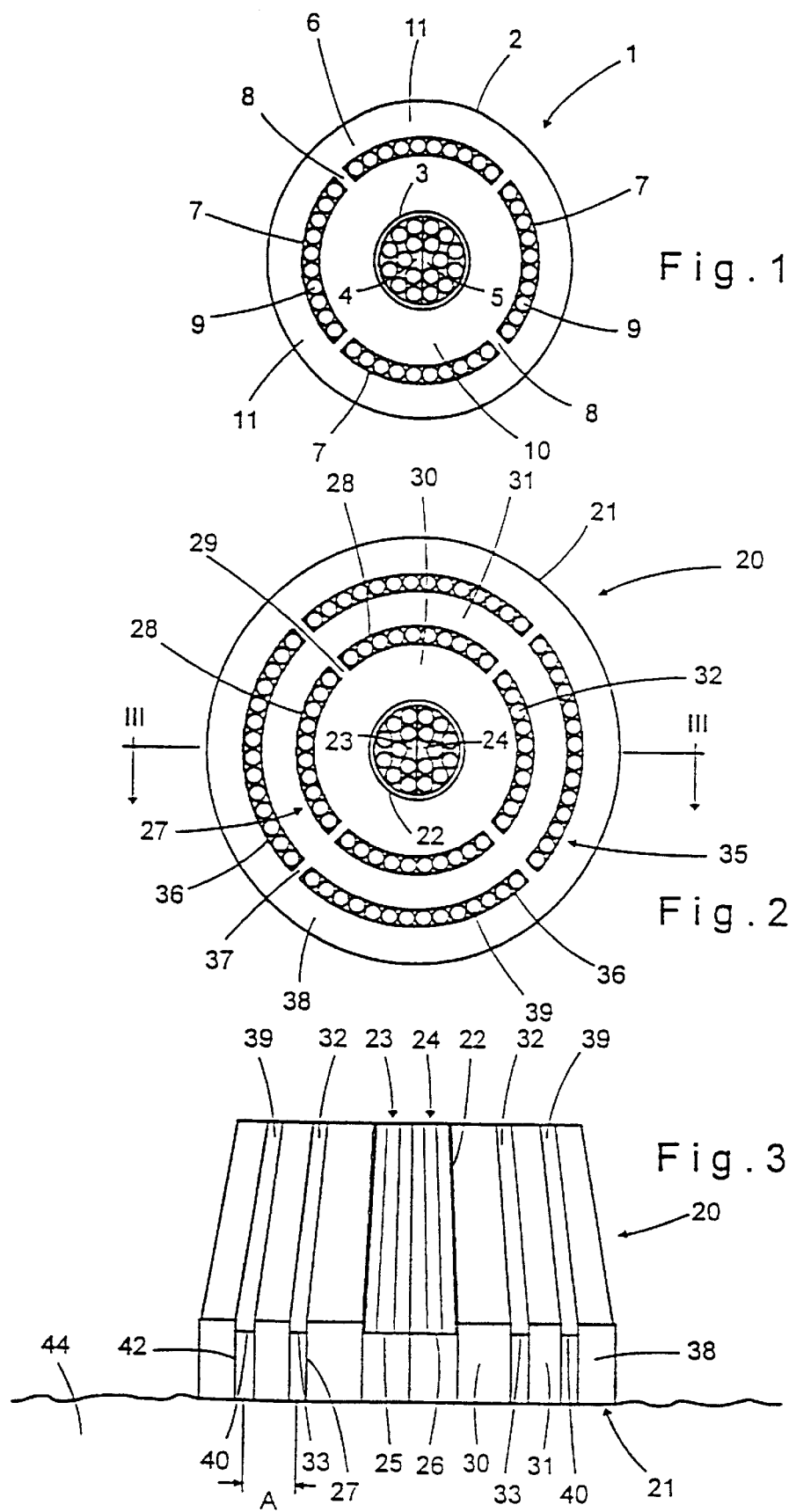

SENSOR, METHOD AND DEVICE FOR OPTICAL BLOOD OXIMETRY

FIELD OF THE INVENTION

The present invention relates to a novel sensor for non-invasive optical blood oximetry, such as blood pulse oximetry effected on a blood perfused tissue; to a method of optical oximetry; and to a device suitable for performing the method.

BACKGROUND OF THE INVENTION

In the prior art there is described a method of measuring the degree of oxygen saturation of blood using what is commonly known as the optical pulse oximetry technology. References to that technology may be found in U.S. Pat. Nos. 4,167,331, 4,938,218, in the brochure "Fetal Oxygen Physiology" sponsored by NELLCOR LTD., and there are others. In accordance with this method, a blood perfused tissue is illuminated and light absorption by the tissue is determined by a suitable light sensor. Pulsatile changes in the value of absorption which are caused by cardiovascular activity of the blood are then used to determine the characteristic of interest, i.e. the degree of blood oxygen saturation.

The value of oxygen saturation ($SaO_2$) in arterial blood is defined by the following known equation:

$$SaO_2 = \frac{[HbO_2]}{[HbO_2] + [Hb]} 100\% \qquad (1)$$

where $[HbO_2]$ is the concentration of oxygenated hemoglobin concentration in a unit of blood volume and $[Hb]$ is the concentration of reduced hemoglobin.

In commonly used methods of pulse oximetry a tissue under investigation is illuminated by light having at least two components of different wavelengths, and the measurements are based upon the following two physical phenomena:

(a) the light absorbance of oxygenated hemoglobin is different from that of reduced hemoglobin, at each of the two wavelengths;

(b) the light absorbance of the blood perfused tissue at each wavelength has a pulsatile component, which results from the fluctuating volume of arterial blood passing across the tissue between the light source and the sensor.

It is therefore assumed, that the pulsatile absorbance component of a tissue layer located between the light source and the sensor characterizes the degree of oxygen saturation of arterial blood.

Various types of sensors designed for effecting measurements in the performance of optical pulse oximetry are known in the art, and among the known optical sensors those dedicated to measuring the degree of oxygen saturation of fetal arterial blood constitute a particular group of such devices.

Basically, the prior art discloses two types of optical sensors which are associated with and serve for two modes of performing optical blood oximetry: transmission pulse oximetry in which so-called transmissive sensors are used and reflection pulse oximetry in which so-called reflectance or transflectance sensors are used. In transmission pulse oximetry one measures light passing across a blood perfused tissue such as a finger, an ear or the like by placing a light emitter and the detection of a transmissive sensor at two opposite sides of the tissue under examination, as described for example in U.S. Pat. No. 4,938,213. In reflection oximetry, on the other hand, reflectance or transflectance sensors can be used which comprise both light emitters and light detectors which are accordingly placed on one and the same side of the tissue under examination, as described, for example, in U.S. Pat. Nos. 5,228,440, 5,247,932, 5,099,842 and in WO 90/01293. Reference to the two types of sensors can also be found, for example, in U.S. Pat. No. 5,247,932 and in "Fetal Oxygen Saturation Monitoring" sponsored by NELLCOR.

Both the transmission and the reflection modes of operation have specific limitations of applicability and their accuracy in general, and in specific applications in particular is not satisfactory. This, for example, the transmission technology can be successfully applied only in cases where the tissue to be investigated forms a distinctive protrusion which makes it possible to apply a light emitter and a light sensor at opposite surfaces.

It is thus evident that the reflection technology is the one most commonly resorted to, notably in fetal oximetry. Unfortunately, however, accuracy of the conventional reflection technology is rather low in comparison with that of the transmission one, because the degree of diffusion of the emitted light in the tissue is unknown, which means that the nature of the functional interdependence between a light signal received by the sensor and the degree of blood oxygen saturation is also unknown. Another disadvantage of the known reflection technology is a partial shunting of the emitted light on the surface of the tissue between the source and the sensor, and a specular reflection created by the superficial layer of the tissue.

U.S. Pat. No. 5,009,842 describe a sensor with means for overcoming the problem of shunting of the emitted light on the outer surface of the tissue between the light source and the detector. U.K. Patent Application No. 2 269 012 proposes to select and separate light signals resulting from light reflection by a superficial layer of a blood perfused tissue such as skin or hair, essentially by choosing a particular distance between the locations of emitting and detecting optical fibers on the contacted surface of the tissue under examination.

Fetal oximeters usually comprise applicators which generally include a plate with at least one substantially point-like light source and at least one substantially point-like light detector suitably spaced from the light source(s). One drawback of such applicators is that if the applicator is applied to a non-uniform section of the skin, such as a hairy portion or a birthmark, the light signal received by the detector(s) will be distorted. Even in relatively large size oximetry, e.g. of the kind described in U.S. Pat. No. 5,099,842 the light sources and detectors are still point-like and accordingly it is practically unadvoidable for an operator to apply it to a wrong portion of the skin of a fetus.

It is important to recall that the basic assumption underlying the theory of transmission and reflection oximetry is, that optical paths of light rays with different wavelengths emitted in the tissue by different light sources, are substantially equal. However, in actual fact the length of such an optical path depends on the light scattering coefficient which, in its turn, is a function of the wavelength. Accordingly, when the wavelengths of the light sensors chosen for oximetry measurements and with them the light scattering coefficients significantly differ from each other, the basic assumption of substantial equivalence of optical paths is violated.

In cases where two or more point-like light sources are used, problems may arise due to the fact that the skin surface, blood vessels and other parts of biological media, are not structured and distributed homogeneously. Thus, if one point-like light source emitting at a given wavelength is applied to any site of a non-uniform skin, while the other light source emitting at a different wavelength is attached to a topographically adjacent but optically different site, then in consequence of different light scattering and absorption at the two distinct wavelengths, which occurs from the very beginning, the optical paths of the light emitted by the two sources cannot be equal. The total amount of optical energy acquired by a detector can be approximated as being the sum of the amounts of energy portions carried by the propagating rays reaching the detector. As the optical paths of these rays are wavelength-dependent and since each part of that energy travels to the detector through a different optical path, the total attenuation of light components with different wavelengths can significantly differ from each other, with the consequence of the occurrence of a random error in the evaluation of oxygen blood saturation.

Another drawback of known sensors for blood oximetry is that they utilize LEDs as light sources for illuminating a tissue with light having two wavelength components. The LED light sources are either installed in the probe itself such as, for example, in U.S. Pat. No. 4,938,218 or linked to the probes via optical fibers such as, for example, in U.S. Pat. No. 5,099,842, GB-A-2 269 012, WO 91/18549 and WO 90/01293. such light sources may provide, for example, a pair of wavelengths of 700 nm and 800 nm which are suitable for the purposes of blood oximetry. However, although it is well known that the accuracy of oximetric measurements increases the closer the two wavelengths are to each other, nevertheless within the wavelength range required for oximetry LEDs are incapable of providing two wavelengths closer to each other than 100 nm.

GENERAL DESCRIPTION OF THE INVENTION

Against the above background it is an object of the present invention to provide a novel sensor for optical blood oximetry, free of the disadvantages of known technologies.

It is a further object of the invention to provide a novel method of optical blood oximetry.

It is yet another object of the invention to provide an apparatus for the performance of optical blood oximetry embodying the novel sensor and a method making use thereof.

Essentially, the objects of the present invention are achieved by ensuring that the light paths of light components with different wavelengths, emitted by at least two distinct light emitters, will always be substantially equal to each other irrespective of the nature of the skin and of the underlying tissue and also irrespective of variations in physiological conditions.

According to one aspect of the present invention there is provided a sensor for noninvasive optical blood oximetry, comprising a carrier body with an applicator block having a contact surface which in operation faces a blood perfused body tissue of a subject under investigation, which applicator block is fitted with at least two point-like light emitters positioned in close proximity to each other and emitting each light at a wavelength distinct from that of the other, and at least a first, essentially annular light detector terminal concentrically surrounding said at least two light emitters, coupled to a light detector device and having a free, light-acquiring end for the acquisition of light arriving from said body tissue.

It has been found that even if a sensor according to the invention is placed on to the skin without fine adjustment, at least a portion of the annular detector will contact the skin without encountering any intervening opaque obstacles, and consequently an emitted light signal will, after passing through the tissues, be acquired by the detector terminal. In other words, the signal-to-noise ratio of a sensor according to the present invention is significantly improved due to the specific novel configuration of the detector terminal and the geometry of the sensor.

It should be noted, that due to the essentially annular, i.e. axisymmetric configuration of the first detector in a sensor according to the invention, any local disturbances in the tissue structure which in case of a prior art point-like detector would result in significant deviation of the optical path, will not affect the intrinsic average optical path of light of a given wavelength. Put in other words, the annular shape of the detector and the geometry of the sensor ensure the stability of the optical paths for each given wavelength.

In a preferred embodiment of the invention the applicator block has a second essentially annular light detector terminal spaced from and concentric with said first light detector terminal. With a sensor having such a configuration it is possible to perform a modified, new method of evaluation of blood oxygen saturation, as will be described further below.

The said light emitters may each be a light source positioned within the applicator block, or alternatively a light emitter terminal having a free, light emitting end and being coupled via another end to a light source. Typically the light emitter terminals are in form of bundles of optical fibers.

The light detector terminals preferably consist of a plurality of optical fibers having each one free, light-acquiring end and coupled via another end to a light detector device.

The provision that the light emitting ends of the light emitter terminals should be point-like means that they should each have a small area. Typically the two terminals will be complementary to each other forming together a circular plate having a diameter of the order of 1 mm.

The light detector(s) of a sensor according to the invention may, for example, comprise a plurality of photo-diodes. Examples of light sources in a sensor according to the present invention are laser diodes capable of producing at least two distinct powerful monochromatic light radiation with very close wavelengths, within the range of from 670 to 940 nm and preferably 750 to 800 nm, differing from each other by say, 10–20 nm. Thus, in a preferred embodiment a first laser diode emits at 750–760 nm and a second laser diode at 780–800 nm. Such characteristics are not available in light sources, such as LEDs used in conventional oximetry apparatuses. The laser diodes have the further advantage of enabling a more linear absorption by the tissues of monochromatic light of any wavelength within the intrinsic emission range.

In view of all this, the use of laser diodes in the optical sensors according to the invention enables to fulfill a basic requirement of oximetry, namely the optical paths equivalence at different wavelengths of radiation.

Preferably the carrier body of a sensor according to the invention is opaque.

In one embodiment, said applicator block in a carrier body of a sensor according to the invention comprises an axial, throughgoing bore perpendicular to said contact surface and holding said light emitter terminals, and a least one substantially annular space concentrically surrounding said bore and accommodating each a light detector terminal.

In one particular design of a sensor according to the foregoing embodiment each light detector terminal is placed within said substantially annular space of said applicator block such that the free light acquiring ends thereof are sunk within the accommodating annular space and removed from said contact surface, whereby a free portion of said annular space constitutes a collimator that rejects specular reflection. The distance by which the free ends are removed from the contact surface is so selected, that only light arriving from a relatively deep layer of the blood perfused tissue and directed substantially parallel to the axis of the applicator block is acquired, while the specular reflection from the superficial layer of the tissue, which is substantially divergent from the axis, is rejected.

It has been found that an increase of the distance between a point-like light emitter terminal and a detector terminal helps not only to overcome the shunting effect, but also to improve the sensitivity of the sensor. On the other hand, however, the intensity of the detected signal drops with an increase of the distance between the light emitter and detector terminals, which puts a practical limitation on the distance between the emitter and detector terminals. An additional limitation results from the requirement of clinicians to minimize the size of the sensor, especially for neonatal and fetal monitoring applications.

In a preferred embodiment of the invention, each light detector terminal comprises optical fibers with obliquely cut light-acquiring ends. In this way the sensitivity of the sensor is improved whereby a working light signal reflected from even relatively deep and remote layers of the tissue under investigation can be perceived.

According to the above embodiment it is further preferred that at least one of the annular spaces holding said first and second annular detector terminals are slanting with their side walls flaring out towards the contact surface such that the said obliquely cut light-acquiring ends of the detector terminal constituting optical fibers are flush with or parallel to the contact surface.

It is known from the prior art, that an optical fiber with an obliquely cut light-acquiring end generally rejects light rays arriving at a part of the end close to the shorter side wall of the fiber and acquires light rays arriving at a part of the end closer to the longer side wall. However, there is no indication in the prior art, that such optical fibers have ever been used in sensors for optical blood oximetry.

In the sensor set out above the geometry of the optical fibers enables to increase the area of the tissue at which the light detector terminals may still acquire working optical signals. Where in accordance with the invention the optical fibers that constitute an annular light detector terminal have obliquely cut light-acquiring ends, the terminal is capable of acquiring working signals from an annular detection zone of the tissue that has a larger inner radius than that of the detector terminal ring.

Due to their specific construction, the light detector terminals described hereinabove reject the slanting light rays appearing between the light emitter and light detector terminals, while at the same time enhancing the acquisition of light coming out from relatively deep blood perfused layers of the tissue. Accordingly, such a sensor has an improved sensitivity without it having been necessary to increase the distance between the light emitter and detector terminals and consequently also with no need to increase the prescribed limited size of the sensor body.

In a preferred embodiment of the above sensor, the detector terminal constituting optical fibers each have an obliquely cut, light-acquiring end inclined towards a plane perpendicular to the longitudinal fiber axis by an acute angle. In case of plastic optical fibers this acute angle does not exceed about 42°, and is preferably within the range of about 20°–22°.

The carrier body of the sensor may be of any suitable shape, e.g. cylindrical, and holds at one end the said applicator block so that the contact surface of the latter forms one end face of the body.

As mentioned, in transmission pulse oximetry the emitted light passes between opposite surfaces of the blood perfused tissue under investigation, while in reflection pulse oximetry light emission and detection occur at the same surface of the tissue. In both the transmission and reflection methods, pulsatile changes of the value of absorption of the light by the blood perfused tissue are used to determine the characteristics of interest, the pulsatile changes being conventionally determined on the basis of the relationship between the intensity of the emitted light and that of the light detected by a single detector.

In accordance with the present invention, a novel approach has been conceived by which the pulsatile changes are determined, on the basis of measured relation between intensities of light acquired by at least one pair of detector terminals differently distanced from the light emitting terminals. In this method, the detector terminal closest to the emitter terminals may be considered with respect to the second, more distanced detector terminal as a quasi light emitter terminal.

This approach is based on the following physical model. A photon, after travelling a certain distance in a sample, is randomly scattered. This process is repeated until the photon leaves the sample boundaries. The photon travelling in the initial direction is considered as "transmitted" photon; the photon moving in the opposite direction is a "reflected" photon. After 30 to 40 steps any "memory" of the direction of the incident radiation is lost and there is no preferred direction of propagation, the light intensity decreasing isotropically in all directions. This interpretation of the light propagation behavior enables to apply to the reflectance oximetry the well known Lamber-Beer law which is used in the transmission oximetry, but for a radial direction.

In the context of the above novel method, the novel sensor embodiment in which the light detector terminals are arranged in two concentric rings around the light emitter terminals, the detector terminals define between them a tubular section of the tissue which is quasi-transmissively illuminated by light emanating from the emitters. Accordingly, such a sensor according to the invention may be described as a reflectance sensor that simulates a transmissive one.

It is to be noted that in a sensor according to the invention having two concentric detector terminals, the optical paths of illumination provided by the two real emitter terminals are similarly affected by any kind of optical disturbance in the annular detection zone, independent of the wavelength of the emitted light and of the distance of the emitter terminals from the first annular detector terminal. Accordingly, substantial equivalence of optical traces will automatically be achieved for any location of the sensor on the skin and also in case of changing physiological conditions in the underlying tissue.

Thus by another aspect the invention provides a method of noninvasive optical blood oximetry in blood perfused tissues including:

provinding an optical sensor with an applicator block holding at least two light emitters in close proximity to each other and at least two light detector terminals concentrically surrounding said at least two light emitters and having a contact surface;

positioning said applicator block on a skin portion of a subject where the underlying tissues are to be investigated, with the contact surface facing the skin;

sequentially emitting from said emitters, light of at least two different wavelengths;

detecting the intensity of light signals arriving from the tissues under investigation by integral acquisition thereof through said at least two light detector terminals;

determining the ratios between the intensity of light detected by said at least two annular light detector terminals at each of said at least two different wavelengths; and determining a value of oxygen saturation of the blood on the basis of such ratios.

In the applicator block used in the performance of the above method the said light emitters may each be a light source positioned within the applicator block, or alternatively a light emitter terminal having a free, light emitting end and being couple via another end to a light source. Typically the light emitter terminals are in form of bundles of optical fibers.

The above method is applicable for determining oxygen saturation in the arterial blood. In this application it is assumed that a pulsatile component of the light absorbance at each one of the wavelengths results from the fluctuating volume of arterial blood in the tissue section between the first light detector and the second light detector, and therefore this pulsatile absorbance component is indicative of the degree of oxygen saturation.

In the performance of the above method two sets of measurements are effected at two points of time, the first being the nil (minimum) point and the second being the crest (maximum) point of the pulsatile arterial blood pressure component. Each of these two sets of measurements include the following two steps assuming that the tissue is illuminated by light of two different wavelengths, and that the sensor has only two detector terminals:

Step 1—The tissue is illuminated with light of the first wavelength, while light of the second wavelength is off, and light signals are recorded simultaneously by the first and second detectors;

Step 2—The tissue is illuminated with light of the second wave length, while the light of the first wavelength is off, and light signals are recorded simultaneously by the first and second detectors.

The procedure pursuant to these measurements comprises:

determining two intensity ratios for each of the said two points, the first intensity ratio being between the light signal intensities registered by the first and second light detectors at the second wavelength, and the second intensity ratio being between the light signal intensities registered by the first and second light detectors at the second wavelength;

computing first and second pulsatile components AC1 and AC2 of the light signal for each of said first and second wavelengths, being each the difference between the intensity ratio calculated at the crest and the nil points for the respective wavelength;

computing first and second constant components DC1 and DC2 of the light signals for each of said first and second wavelengths, being each the average of two intensity ratios calculate at the nil and crest points for the two wavelengths; and calculating the oxygen saturation of arterial blood $SaO_2$ in accordance with the following equation:

$$SaO_2 = K1\frac{AC1 \times DC2}{DC1 \times AC2} + K2 \qquad (2)$$

where K1 and K2 are calibration constants.

The departure of the present invention from the prior art will be readily appreciated by a person skilled in the art, when comparing with each other equation (1) and (2) herein.

According to yet another aspect of the invention there is provided an apparatus for noninvasive optical blood oximetry comprising:

a sensor having a carrier body with an applicator block having a contact surface which in operation faces a blood perfused body tissue of a subject under investigation, which applicator block is fitted with at least two point like light emitters positioned in close proximity to each other and each emitting light of a wavelength distinct from that of the other; and at least two, essentially annular light detector terminals concentrically surrounding said at least two light emitter terminals, having a free, light-acquiring end for the acquisition of light arriving from a tissue under investigation;

at least two light sources coupled to said light emitter terminals and capable of emitting light at at least two different wavelengths;

at least two optical detectors coupled to said at least two, essentially annular detector terminals;

control means adapted to cause said at least two light sources to illuminate said tissue sequentially via said emitter terminals and to obtain synchronized measurements of intensity of light acquired by said at least two detectors via said at least two detector terminals; and processor means for determining characteristics of interest from the results of said synchronized measurements.

In accordance with one embodiment the said light emitters are light sources positioned within the applicator block.

In accordance with another embodiment the light emitters consist of a plurality of optical fibers having each one free, light-acquiring end and coupled via another end to a light detector device.

BRIEF DESCRIPTION OF THE DRAWINGS

For better understanding the invention will now be further described and illustrated by way of non-limiting examples only, with reference to the annexed drawings in which:

FIG. 1 is an enlarged schematic plan view of one embodiment of an applicator block in a carrier body of a sensor according to the invention;

FIG. 2 is an enlarged schematic plan view of another embodiment of an applicator block;

FIG. 3 is a cross-section taken line III—III of FIG. 2;

DETAILED DESCRIPTION OF SOME PREFERRED EMBODIMENTS

Figure 4:
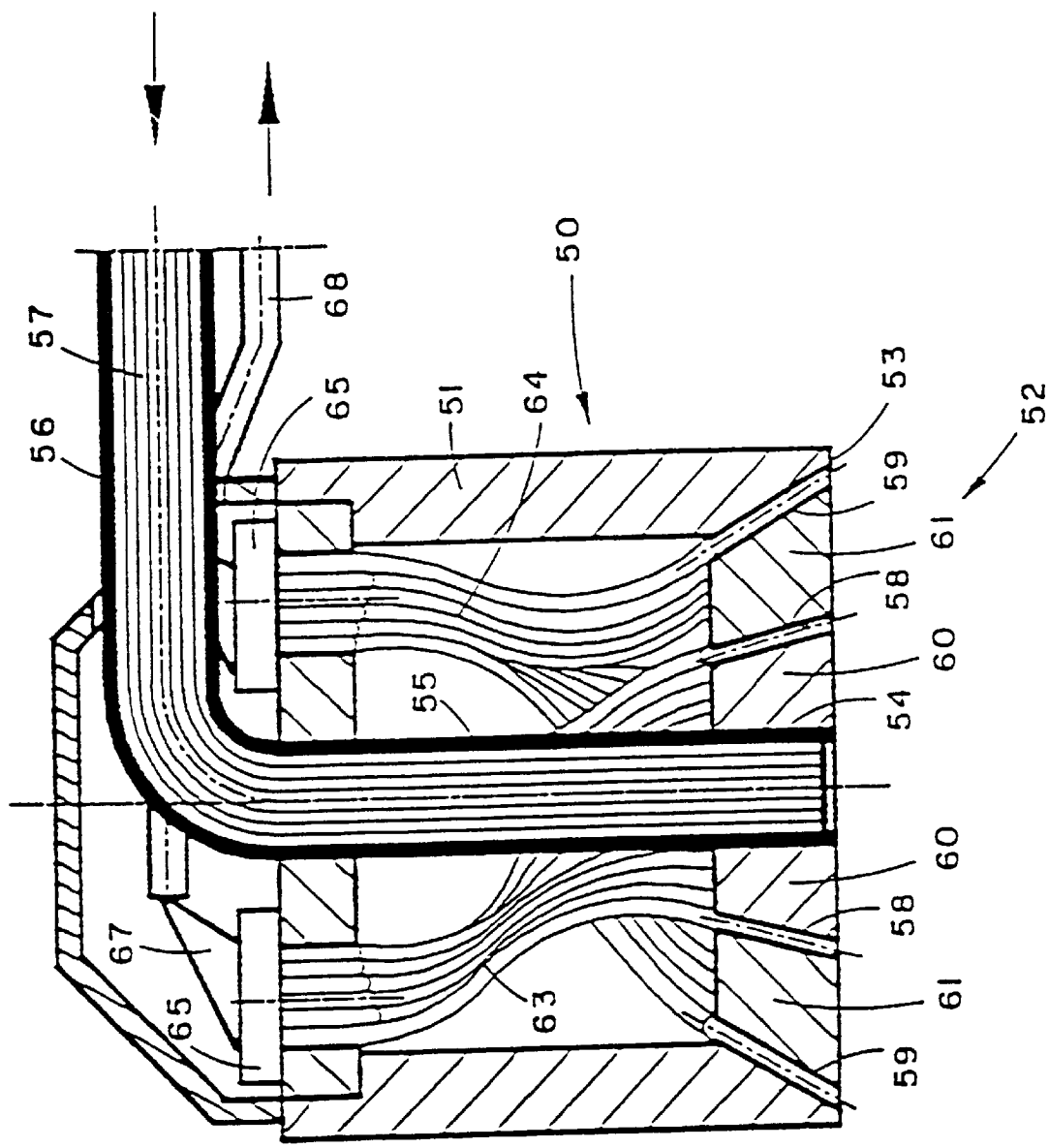
FIG. 4 is an enlarged axial cross-sectional view of a further embodiment of a carrier body with applicator block in a sensor according to the invention.

FIG. 1 shows the contact surface of an applicator block of a carrier body in a sensor according to the invention. As shown, block 1 which is assumed to be made from an opaque material such as a metal, has a contact surface 2 and a central bore 3 holding two bundles of optical fibers 4 and 5 serving as light emitter terminals. Bundles 4 and 5 are coupled each to a laser diode (not shown) and are thus capable of emitting light at two distinct wavelengths. An essentially annular space 6 provided in block 1 and consisting of a number of segments 7 with intermittent braces 8 concentrically surrounds the central bore 3 and accommodates a plurality of optical fibers 9 forming together an annular light detector terminal. Inside the sensor's carrier body optical fibers are assumed to be bundled together in a manner not shown and are coupled to a detector device, e.g. a photodiode, equally not shown.

Braces 8 of block 1 connect the median section 10 and the peripheral section 11 of the block with each other.

The light-acquiring ends of the light detector constituting optical fibers 9 may either be flush with the contact surface 2 or alternatively be removed from the surface inwards by a desired distance.

In operation the two light emitter terminals 4 and 5 emit light on to a tissue under investigation, and the detector (not shown) transforms and modulates the light acquired by the light-acquiring ends of the optical fibers 9 into an electric signal suitable for further processing.

FIGS. 2 and 3 illustrate schematically another embodiment of an applicator block in a carrier body of an optical sensor according to the invention. As shown, an applicator block 20 has a contact surface 21 and a central bore 22 holding two bundles 23 and 24 of optical fibers which constitute two light emitter terminals and which are connected to a pair of light sources (not shown). As shown, the light emitting ends 25 and 26 of the light emitter terminals 23 and 24 are withdrawn inside bore 22 and are thus removed from the contact surface 21.

Block 20 further comprises a first annular space 27 concentric with bore 22 and consisting of four segments 28 with intermittent bracing members 29 linking with each other the core section 30 and median section 31 of block 20. The first annular space 27 houses a plurality of optical fibers 32 constituting together a light detector terminal and have each a light-acquiring end 33.

A second annular space 35 surrounds concentrically the first annular space 27 and similar to the latter consists of four segments 36 with intermittent bracing members 37 connecting the median block section 31 with a peripheral section 38. The second annular space 35 houses a plurality of optical fibers 39 which together constitute a second light detector terminal and have each a light-acquiring end 40. As shown in FIG. 3 the light-acquiring ends 40 are removed from the contact surface 21. The empty portion 41 of the annular space 27 and 42 of the annular space 35 serve as collimators for light returning from a tissue under examination.

As seen in FIG. 2, each of the two light emitting terminals 23 and 24 is hemi-circular, the two terminals being complementary and form together a circular plate having a diameter of say 1 mm. The diameters of the first and second annular spaces may respectively be 5 and 7 mm.

The two light emitter terminals are linked to two distinct light sources (not shown) generating light of different wavelengths and the two light detector terminals constituted by the optical fibers 32 and 39 located respectively in the annular spaces 27 and 35, are linked to optical detector devices (not shown).

In operation sensor 20 is applied to a skin portion above a tissue 44 which is sequentially illuminated via the light emitting terminal by the two light sources which are not shown and which may, for example, be laser diodes emitting light at the two wavelengths of about 750 and 780 nm. The light is absorbed and partially reflected by the tissue and the pulsatile changes of the light absorption in the annular section A of tissue 44 may be estimated by comparing the integral light signal received by the first light detector terminal constituted by the optical fibers 32 with the integral light signal received by the second light detector terminal constituted by the optical fibers 39. A ratio of the intensities of these integral signals characterizes a degree of attenuation of the light in the annular section A of the tissue, for a specific wavelength. The mentioned ratio obtained for each of the applied wavelengths are then used for determining the desired characteristics such as the oxygen saturation of the blood in the tissue 44.

FIG. 4 illustrates schematically an axial cross-sectional view of a modified sensor 50 comprising an opaque, generally cylindrical body 51 having an applicator block 52 with a contact surface 53. Block 52 has a central axial bore 54 holding the lower end portion of a tube 55 merging into a horizontal portion 56 and accommodating one optical fiber bundle marked 57, guiding at least two light sources (not shown) to light emitting terminals.

Block 52 further comprises first and second annular slots 58 and 59 concentric with bore 54, adjacent block and body portions being suitably linked to each other in a manner not shown. The slots 58 and 59 are slanting, flaring out in the direction of the contact surface 53 such that the adjacent block portions 60 and 61 have frusto-conical shapes as shown. Slots 58 and 59 accommodate the free, light-acquiring ends of first and second optical fiber bundles 63 and 64 which constitute first and second detector terminals and pass through the inner space of body 51 to photodetectors 65 electrically connected through wires 67 to a cable 68. Each of the light-acquiring ends of the optical fibers of bundles 63 and 64 terminates with an oblique cut, forming an acute angle with the axis of the fiber such that the light-acquiring end of each fiber is either flush with or parallel to the contact surface 53.

In operation the outer end portion of tube 56 is coupled to two light sources (not shown).

Figure 5:
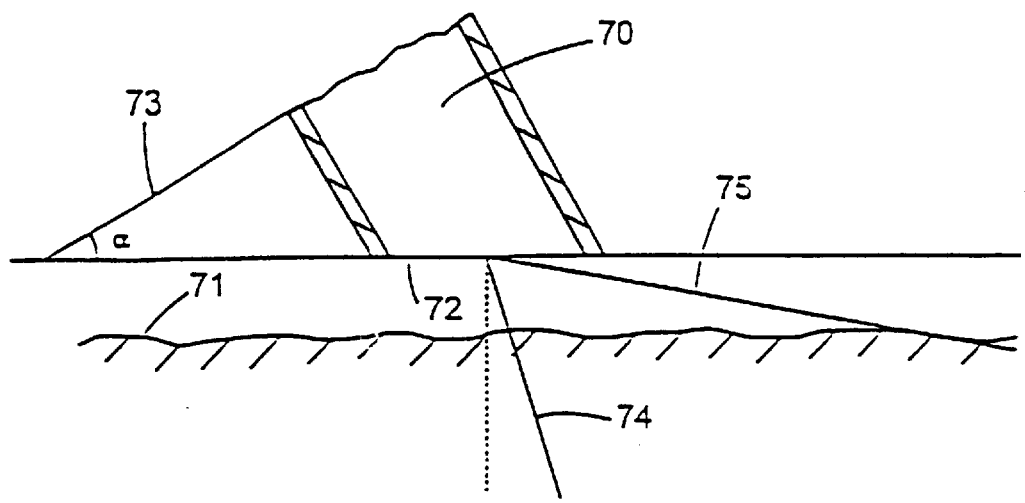
FIG. 5 is a diagram explaining the optics at the light-acquiring end of one embodiment of an optical fiber in a light detector terminal of a sensor according the invention.

FIG. 5 schematically illustrates a scope of vision of an optic fiber 70 which faces a surface 71 of a tissue with its obliquely cut surface 72. Fiber 70 is assumed to form part of the bundle 63 in FIG. 4. The fiber 70 is characterized by an acute angle α formed between the cut end face 72 and a plane 73 perpendicular to the fiber's axis. The actual scope of vision of the fiber 70 extends between a left-hand ray 74 and a right-hand ray 75 and may be calculated from the angle α and the optical parameters of the fiber. As will readily be understood by those skilled in the art, the specular reflection and shunted light which mostly come to the surface 72 from left of the ray 74 will not be perceived by the detector. On the other hand, the detector will perceive light arriving from the reflective deep layers of the tissue in directions substantially perpendicular to surface 71 in a rather wide area confined between rays 74 and 75. As one can see, the scope of vision of the cut-ended optic fiber 70 is shifted in the direction of its longer side wall portion. It has been found by the inventors, that the fiber 70 is adequate when the angle α is not greater than about 42°, and is most effective when the angle α is within the range of from about 20° to about 22°. More particularly, an oblique cut with an angle α of about 20° to about 22° also increases sharply the distance of vision.

Figure 6:
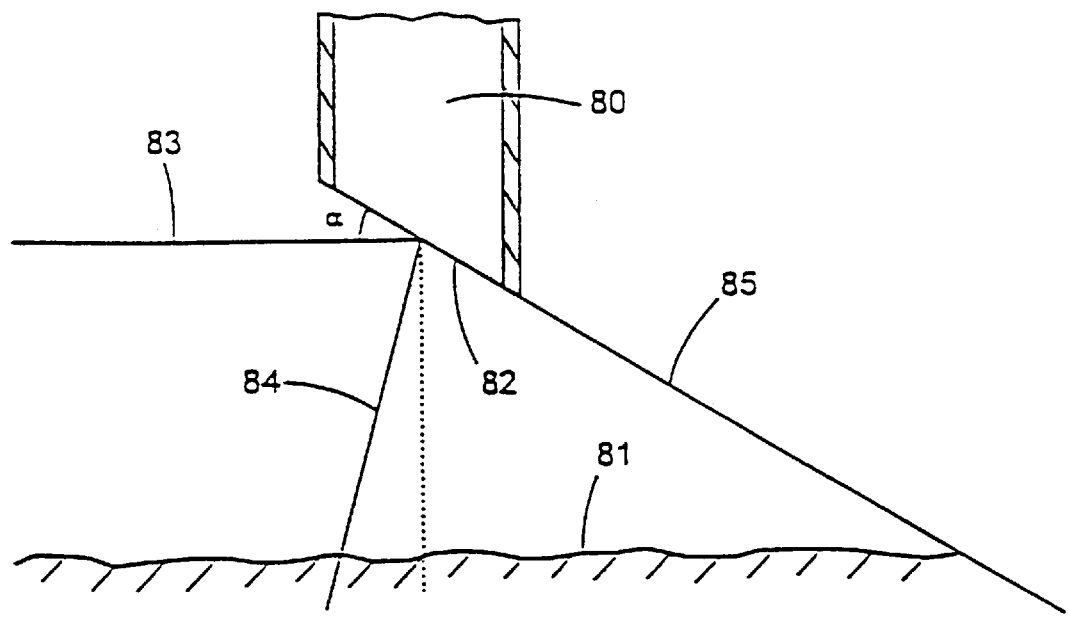
FIG. 6 is a similar diagram concerning another embodiment of the light-acquiring end of an optical fiber.

FIG. 6 is a schematical illustration of a cut-ended optical fiber 80 which, in distinction from fiber 70 in FIG. 5, the fiber axis is perpendicular to a surface 81 of a tissue. However, the oblique cut 82 of the fiber 80 while facing the surface 81, is not parallel to it, an acute angle α being formed between the surface 82 of the cut and a plane 83 that is parallel to surface 81 and accordingly perpendicular to the fiber's axis. Similar as in the embodiment of FIG. 5, angle α determines the scope of vision of the fiber 80, which is defined by a left-hand beam 84 and a right-hand beam 85. In analogy to the fiber of FIG. 5, the scope of vision of the cut-ended optic fiber 80 is shifted from the shorter to the longer side wall. The same limitations to the value of angel α apply as in FIG. 5.

Figure 7:
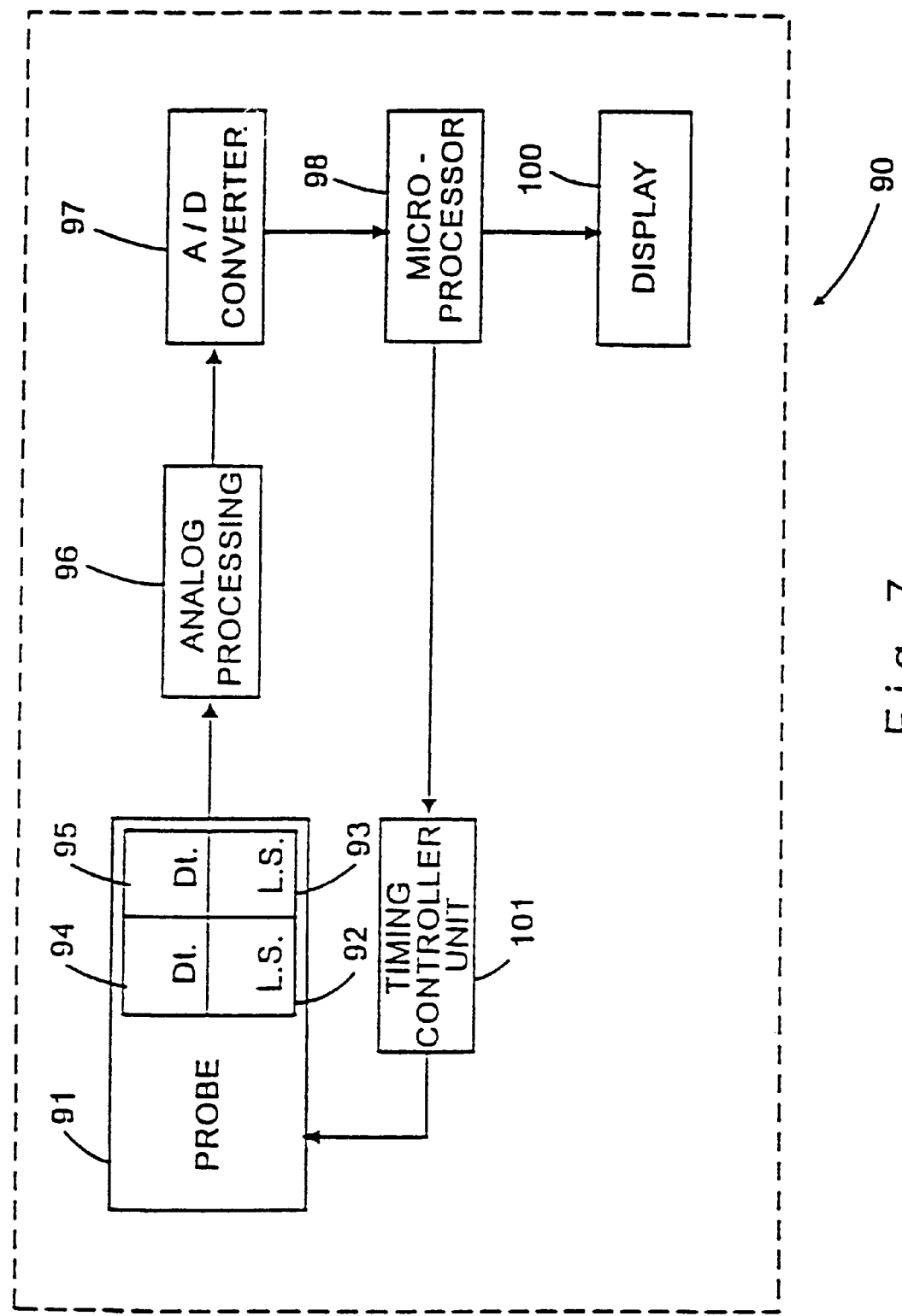
FIG. 7 is a block diagram of an oximeter according to the invention.

FIG. 7 is a block diagram of one embodiment of an oximeter 90 according to the invention. As shown, the oximeter 90 comprises a probe 91 including two light sources 92 and 93, e.g. two laser diodes generating light of two different wavelengths for the sequential illumination of a tissue under investigation. The probe further comprises two photodetectors 94 and 95. The light signals received from the two light detectors 94 and 95 are transformed and modulated into electric signals which are amplified by an analogue processing unit 96, digitized by an A/D converter 97 and transmitted to a microprocessor 98 for computing the characteristic of interest which is displayed on a display 100. Light sources 92 and 93 of probe 91 are controlled by the microprocessor 98 via a timing controller unit 101.

The procedure of measurement of the characteristic of interest by the oximeter 90 is as follows.

The calculations are performed at two points of time on a pulsating light intensity graph, representing the pulsatile arterial blood component, the first being the nil (minimum) point, and the second the crest (maximum) point thereof. The measurements and calculations include the following six steps:

(a) first light source 93 ON and second light source 93 OFF—first signals of a first wavelength are recorded by each of the first and second detectors 94 and 95;

(b) second light source 93 ON and first light source 92 OFF—second signals of a second wavelength are recorded by each of the first and second detectors 94 and 95;

(c) both light sources OFF—ambient light is recorded by the first and second detectors 94 and 95;

(d) the detected signals are sequentially filtered and amplified by the analogue processing unit 96 in order to reduce the noise and the ambient light components;

(e) the analogue-to-digital (A/D) converter 97 receives a sequence of signals from the analogue processing unit 96 for digitization and the resulting digital signals are transmitted to the microprocessor 98;

(f) the microprocessor 98 performs digital extraction of DC and AC signal components and calculates the SaO$_2$ according to the following algorithm:

For each of the two calculations two intensity ratios N and M are determined at the two different points of time, namely N1 and N2 for the nil point and M1 and M2 for the crest point of the pulsatile arterial blood pressure component. The first intensity ratios N1 and M1 for the two points are based on the light signals' intensities registered by the first and second light detectors at the first wavelength and the second intensity ratios N2 and M2 for the two points are based on the light signals' intensities registered by the first and second detectors at the second wavelength.

For each of the two wavelengths a characteristic AC of a pulsatile component of the signal is defined, namely AC1 for the first wavelength and AC2 for the second wavelength, each of AC1 and AC2 being the difference between the intensity ratios calculated, respectively, for the crest and nil points at that particular wavelength.

For each of the two wavelengths the characteristic DC of a constant component of the signal is computed, namely DC1 for the first wavelength and DC2 for the second wavelength, each of DC1 and DC2 being the average from two intensity ratios calculated, respectively, at the nil and crest points at a given wavelength.

The microprocessor then calculates:

(i) the ratios R1 and R2 for each of the wavelengths:

$$R_1 = \frac{AC_1}{DC_1}; R_2 = \frac{AC_2}{DC_2}$$

(ii) the ratio $$\gamma = \frac{R_1}{R_2}$$

(iii) the oxygen saturation SaO$_2$ of arterial blood $$SaO_2 = K1 \times \gamma \div K2$$

where $K_1$, $K_2$ are calibration constants.

EXAMPLE

The first light source 92 is a laser diode emitting at 775 nm. and the second light source 93 is a laser diode emitting at 785 nm. The calibration constants of K1 and K2 depend upon geometry and size of detectors and the hemoglobin and oxyhemoglobin absorption coefficients, and are assumed to have the following values:

$$K1=2; K2=0.5;$$

a) First set if measurement at the nil point

1) First light source 92 ON, and second light source 93 OFF—a first signal $I_{11}(1)$ is detected by the first detector 94, amplified and fed into the storage of the microprocessor 98. $I_{11}(1)=1000$.

2) First light source 92 ON, and second light source 93 OFF—a first signal $I_{12}(1)$ is detected by the second detector 95 amplified and fed into the storage of microprocessor 98. $I_{12}(I)=2500$.

3) The intensity ratio N1 for the first wavelength at the nil point, is calculated as follow: $DC_1(1)=I_{11}(1)/I_{12}(1)=1000/2500.=0.4$ 4) Second light source 93 ON, and first light source 92 OFF—a second signal $I_{22}(1)$ is detected by the first detector 94, amplified and fed into the storage of the microprocessor 98 $I_{21}(1)=800$.

5) second light source 93 ON and first light source 92 OFF—a second signal $I_{22}(1)$ is detected by the second detector, amplified and fed into the storage of the microprocessor 98. $I_{22}(1)=2300$.

6) The intensity ratio N2 for the second wavelength at the nil point is calculated as follows: $DC_2(1)=I_{21}(1)/I_{22}(1)=800/2300=0.348$.

b) Second set of measurements at the crest point

7) First light source 92 ON, second light source 93 OFF—a first signal $I_{11}(2)$ is detected by the first detector 94, amplified and fed into the storage of the microprocessor 98. $I_{11}(2)=990$.

8) First light source 92 ON, and second light source 93 OFF—a first signal $I_{12}(2)$ is detected by the second detector 95, amplified and fed into the storage of the microprocessor 98. $I_{12}(2)=2460$.

9) The intensity ratio M1 for the first wavelength at the crest point is calculated as follows: $DC_1(2)=I_{11}(2)/I_{12}(2)=980/2490=0.394$ 10) Second light source 93 ON, and first light source 92 OFF—a second signal of the first detector $I_{21}(2)$ is detected by the first detector 94, amplified and fed into the storage of the microprocessor 98. $I_{21}(2)=780$.

11) Second light source 93 ON and first light source 82 OFF—a second $I_{22}(2)$ is detected by the second detector 95, amplified and fed into the storage of the microprocessor 98. $I_{22}(2)=2400$.

12) The intensity ratio M2 for the second wavelength at the crest point is calculated as follows: $DC_2(2)=I_{21}(2)I_{22}(2)=780/2400=0.325$.

c) Calculation

13) The value AC1, characterizing a pulsatile component for the first wavelength, is calculated as $M1-N1=0.394-0.4=-0.006$ 14) The value AC2, characterizing a pulsatile component for the second wavelength, is calculated as $M2-N2=0.325-0.348=-0.023$ 15) The value DC1, characterizing a constant component for the first wavelength, is calculated as $(N1+M1)/2=(0.4+0.394)/2=0.397$ 16) The value DC2, characterizing a constant component for the second wavelength, is calculated as $(N2+M2)/2=(0.348+0.325)/2=0.337$ The two following ratios for the two wavelengths are calculated:

17) $R1=AC1/DC1=(-0.006/0.397)=-0.015$

18) $R2=AC2/DC2=(-0.023/0.337)0.0068$; and finally

19) $SaO2=K1(R1/R2)+K2=2 \times 0.221+0.5=0,942$

We claim:

1. A sensor for noninvasive optical blood oximetry comprising:
    an applicator body having a contact surface adapted for apposition in contact with a blood perfused body tissue:
    first and second emitters disposed in the applicator body in close proximity to one another and arranged to emit light rays of first and second wavelengths, respectively, to irradiate a first region of the blood perfused tissue, the first wavelength being different than the second wavelength;
    a first waveguide comprising a plurality of light transmitting elements, the first waveguide having proximal and distal endfaces and being disposed in the applicator block surrounding the first and second emitters so that the distal endface is arranged in apposition to a second region of the blood perfused tissue spaced apart from the first region, a portion of the light rays emitted by the first and second emitters being reflected from within the second region, the first waveguide transmitting only light rays reflected from the second region having an angle within a first predetermined range;
    a first detector optically coupled to the proximal endface of the first waveguide, the first detector producing a first electrical output signal corresponding to an intensity of the light transmitted to the first detector via the first waveguide.

2. The sensor as defined in claim 1 wherein the distal endface of the first waveguide defines a frustoconical surface with respect to the plane of the second region.

3. The sensor as defined in claim 2 wherein the frustoconical surface is inclined at an angle less than 42 degrees from the plane of the second region.

4. The sensor as defined in claim 1 wherein each one of the plurality of light transmitting elements has a longitudinal axis inclined at an angle $\alpha$ with respect to a plane normal to the second region and the distal endface of the first waveguide is parallel to the second region.

5. The sensor as defined in claim 4 wherein the angle $\alpha$ is less than about 42 degrees.

6. The sensor as defined in claim 1 further comprising:
    a second waveguide comprising a plurality of light transmitting elements, the second waveguide having proximal and distal endfaces and being disposed in the applicator block surrounding the first waveguide so that the distal endface of the second waveguide is arranged in apposition to a third region of the blood perfused tissue spaced apart from the second region, a portion of the light rays emitted by the first and second emitters being reflected from within the third region, the second waveguide transmitting only light rays reflected from the third region having an angle within a second predetermined range;
    a second detector optically coupled to the proximal endface of the second waveguide, the second detector producing a second electrical output signal corresponding to the intensity of the light transmitted to the second detector via the second waveguide.

7. The sensor as defined in claim 6 wherein the distal endface of the second waveguide defines a frustoconical surface with respect to the plane of the third region.

8. The sensor as defined in claim 7 wherein the frustoconical surface is inclined at an angle less than about 42 degrees from the plane of the third region.

9. The sensor as defined in claim 6 wherein each one of the plurality of light transmitting elements has a longitudinal axis inclined at an angle $\alpha$ with respect to a plane normal to the third region and the distal endface of the second waveguide is parallel to the third region.

10. The sensor as defined in claim 9 wherein the angle $\alpha$ is less than about 42 degrees.

11. The sensor as defined in claim 1 wherein the first and second emitters are light sources.

12. The sensor as defined in claim 1 wherein the first and second emitters are light transmitting elements having proximal and distal ends, each one of the distal ends of the light transmitting elements being a free, light emitting end and each one of the proximal ends of the light transmitting elements being coupled to a light source.

13. The sensor as defined in claim 1 wherein the first waveguide forms an annulus arranged substantially concentrically surrounding the first and second light emitter.

14. The sensor as defined in claim 6 wherein the second waveguide forms an annulus arranged substantially concentrically surrounding the first waveguide.

15. The sensor as defined in claim 1 wherein the first and second light emitters are laser diodes each emitting monochromatic light within a range of 670–940 nm.

16. The sensor as defined in claim 15 wherein the first wavelength is in a range of 750–760 nm and the second wavelength is in a range of 780–800 nm.

17. The sensor as defined in claim 6 wherein the first and second detectors are phototdiodes.

18. The sensor as defined in claim 13 wherein the applicator block includes a portion defining an annular space that accepts the first waveguide, the first waveguide being disposed in the annular space so that its distal endface is retracted from the second region to form an annular gap between the distal endface and the second region, the annular gap serving as a collimator that rejects specular reflection from the second region.

19. The sensor as defined in claim 14 wherein the applicator block includes a portion defining an annular space that accepts the second waveguide, the second waveguide being disposed in the annular space so that its distal endface is retracted from the third region to form an annular gap between the distal endface and the third region, the annular gap serving as a collimator that rejects specular reflection from the third region.

20. A method of noninvasive optical blood oximetry in blood perfused tissues comprising:
   providing an optical sensor with applicator block holding at least two light emitter terminals in close proximity to each other and at least two annular light detector terminals concentrically surrounding said at least two light emitter terminals and having a contact surface;
   positioning said applicator block on a skin portion of a subject where the underlying tissues are to be investigated, with the contact surface facing the skin;
   sequentially emitting from said emitter terminals light of at least two different wavelengths;
   detecting the intensity of light signals arriving from the tissue under investigation by integral acquisition thereof by said at least two light detector terminals;
   determining the ratios between the intensity of light detected by said at least two annular light detector terminals at each of said at least two different wavelengths; and
   determining a value of oxygen saturation of the blood on the basis of such ratios.

21. The method of claim 20, wherein said detecting step comprises simultaneously detecting the intensity of said light signals by said at least two light detector terminals.

22. The method of claim 20, wherein the said light emitter terminals are each a light emitter terminal having a free, light emitting end and being coupled via another end to a light source.

23. The method of claim 22, wherein said light sources are laser diodes each emitting monochromatic light within the range of 670–940 nm.

24. The method of claim 23, wherein a first light source emits at 750–760 nm and a second at 780–800 nm.

25. The method of claim 20, wherein said at least two light detector terminals are connected to first and second light detectors, respectively, further including:
   selecting two points of time for the performance of measurements, a first being a nil point of the pulsatile arterial blood component and a second the crest point thereof;
   performing at each of said first and second points measurements which comprise illuminating with light of a first wavelength and simultaneously recording signals arriving from the tissue with said first and second light detectors, and subsequently illuminating with light of a second wavelength and simultaneously recording signals arriving from the tissue simultaneously with said first and second light detectors;
   determining two intensity ratios for each of said two points of time, the first intensity ratio being between the light signal intensities registered by the first and second light detectors at the first wavelength, and the second intensity ratio being between the light signal intensities registered by the first and second light detectors at the second wavelength;
   computing first and second pulsatile components AC1 and AC2 of the light signal for each of said first and second wavelengths, being each the difference between the intensity ratio caluclated at the crest and the nil points for the respective wavelength;
   computing first and second constatn components DC1 and DC2 of the light signals for each of said first and second wavelengths, being each the average of two intensity ratios calculated at the nil and crest points for the two wavelengths; and
   calculating the oxygen saturation of arterial blood $SaO_2$ in accordance with the following equation:

$$SaO_2 = K1[(AC1 \times DC2)/(DC1 \times AC2)] + K2$$

where K1 and K2 are calibration constants.

26. An apparatus for noninvasive optical blood oximetry comprising:
   a senor having a carrier body with an applicator block having a contact surface which in operation faces a blood perfused body tissue of a subject under investigation, which applicator block is fitted with at least two point like emitter terminals position in close proximity to each other and each emitting light of a wavelength distinct from that of the other, and at least two, essentially annular light detector terminals concentrically surrounding said at least two light emitter terminals, each having a free, light-acquiring end for the acquisition of light arriving from a tissue under investigation;
   at least two light sources coupled to said light emitter terminals and capable of emitting light of a least two different wavelengths;
   at least two optical detectors coupled to said at least two, essentially annular detector terminals;
   control means adapted to cause said at least two light sources to illuminate said tissue sequentially via said emitter terminals and to obtain synchronized measurements of intensity of light acquired by said at least two detectors via said at least two detector terminals; and
   processor means for determining characteristics of interest from the results of said synchronized measurements.

27. The apparatus of claim 26, wherein said control means causes said at least two detectors to simultaneously detect light signals.

28. The apparatus of claim 26, wherein said light sources are positioned within said applicator block.

29. The apparatus of claim 26, wherein each light emitter terminal has a free, light emitting end and is coupled via another end to a light source.

30. The apparatus of claim 29, wherein said light sources are laser diodes each emitting monochromatic light within the range of 670–940 nm.

31. The apparatus of claim 30, wherein a first light source emits at 750–760 nm and a second at 780–800 nm.

* * * * *